United States Patent [19]

Case

[11] 4,033,177
[45] July 5, 1977

[54] DUAL TRACE DISPLAY FOR ULTRASONIC TESTING APPARATUS

[75] Inventor: Dan Frank Case, Bethel, Conn.

[73] Assignee: Automation Industries, Inc., Los Angeles, Calif.

[22] Filed: June 14, 1976

[21] Appl. No.: 696,139

[52] U.S. Cl. .............................................. 73/67.9
[51] Int. Cl.² ........................................ G01N 29/04
[58] Field of Search .......... 73/67.7, 67.8 R, 67.8 S, 73/67.9

[56] References Cited

UNITED STATES PATENTS

3,538,753  11/1970  Gericke ............................ 73/67.9
3,972,228  10/1976  Mansson ........................... 73/67.7

Primary Examiner—Jerry W. Myracle
Attorney, Agent, or Firm—Robert Hockfield

[57] ABSTRACT

An ultrasonic nondestructive testing system is disclosed which is adapted to display test information representing ultrasonic energy reflected from within an object under test in various modes. In one mode, herein called the set-up mode, a dual display is generated. One of the displays contains a portion of the test information effectively expanded along a horizontal scale, while the other display has a contracted horizontal scale thereby to present essentially all of the test signal. In addition, the other display includes a suitable marker to indicate the location and extent of the test information in the first display. In the other, or test mode, the instrument is adjusted to display only the test information shown in the first display of the set-up mode.

6 Claims, 6 Drawing Figures

DUAL TRACE DISPLAY FOR ULTRASONIC TESTING APPARATUS

BACKGROUND

In ultrasonic nondestructive testing it is well known to inspect objects or workpieces by transmitting ultrasonic energy into the workpiece and receiving echoes of the energy reflected from the workpiece. In some forms of ultrasonic equipment, a cathode ray oscilloscope is utilized to display the echo signals or test information as a function of time. This permits the operator to observe the signals visually and to analyze and evaluate the significance of the signals. A considerable amount of the signal is of little, or no, interest to the operator; often a very small segment of the signal representing critical portions of the workpiece is of interest. Accordingly, it is customary to adjust the cathode ray tube so as to expand the display in time whereby only the portion or segment of the signal which is of interest is displayed. The expanded scale permits a more accurate observation and analysis of the test information.

When setting up the instrument, it has seen very difficult to identify positively the particular portion of the test signal which is being effectively magnified by time-expansion and displayed to the operator. It has been possible to adjust the instrument so that the entire test signal is displayed or to adjust it so as to display a particular portion of interest. Frequently, it has been difficult to precisely correlate the two alternate displays, one with the other. This has necessitated a considerable amount of time and careful attention by the operator when setting up the instrument so as to be sure that he has effectively focused the instrument of that part of the test signal which is important. In many instances the test information is extremely complex in its content and this has led to some confusion. As a result, on occasion, the instrument has been focused on immaterial portions of the signal.

SUMMARY

The present invention provides means for overcoming the foregoing difficulties. The invention, as disclosed herein, is particularly adapted to be embodied in ultrasonic nondestructive testing apparatus in which a pulser supplies repetitive electrical pulses to transducer means thereby to transmit ultrasonic energy into a workpiece. The transducer means derives test signals in response to ultrasonic energy reflected from within the workpiece. A cathode-ray display device is provided which includes an image-producing screen, means for projecting a beam of electrons toward the screen and means for deflecting the beam of electrons relative to the screen in first and second directions. Sweep means operative in synchronism with the repetitive electrical pulses supplied to the transducer means is adapted to derive a first sweep signal having repetitive components occurring during time intervals defined by alternate pairs of the repetitive pulses and a second sweep signal having repetitive components ocurring during time intervals defined by remaining pairs of the repetitive pulses, the components of one of the sweep signals having a time rate increase in amplitude different from that of the component of the other of the sweep signals. Means coupling the sweep means to the deflecting means are provided for effecting deflection of the electron beam in the first direction relative to the screen, and means are provided for supplying an electrical signal to the deflecting means for effecting deflection of the electron beam in the second direction relative to the screen in response to electrical signals from the transducer means. Means coupled to the last-named means are provided for deriving an offset signal in synchronism with the repetitive pulses and having one amplitude during the aforesaid alternate pairs of the repetitive pulses and another amplitude during the remaining pairs of the repetitive pulses so as to deflect the electron beam in the second direction relative to the screen between two sections thereof displaced from one another in the second direction thereby to produce a display of reflected energy signals in each of the sections.

DESCRIPTION

Figure 1:
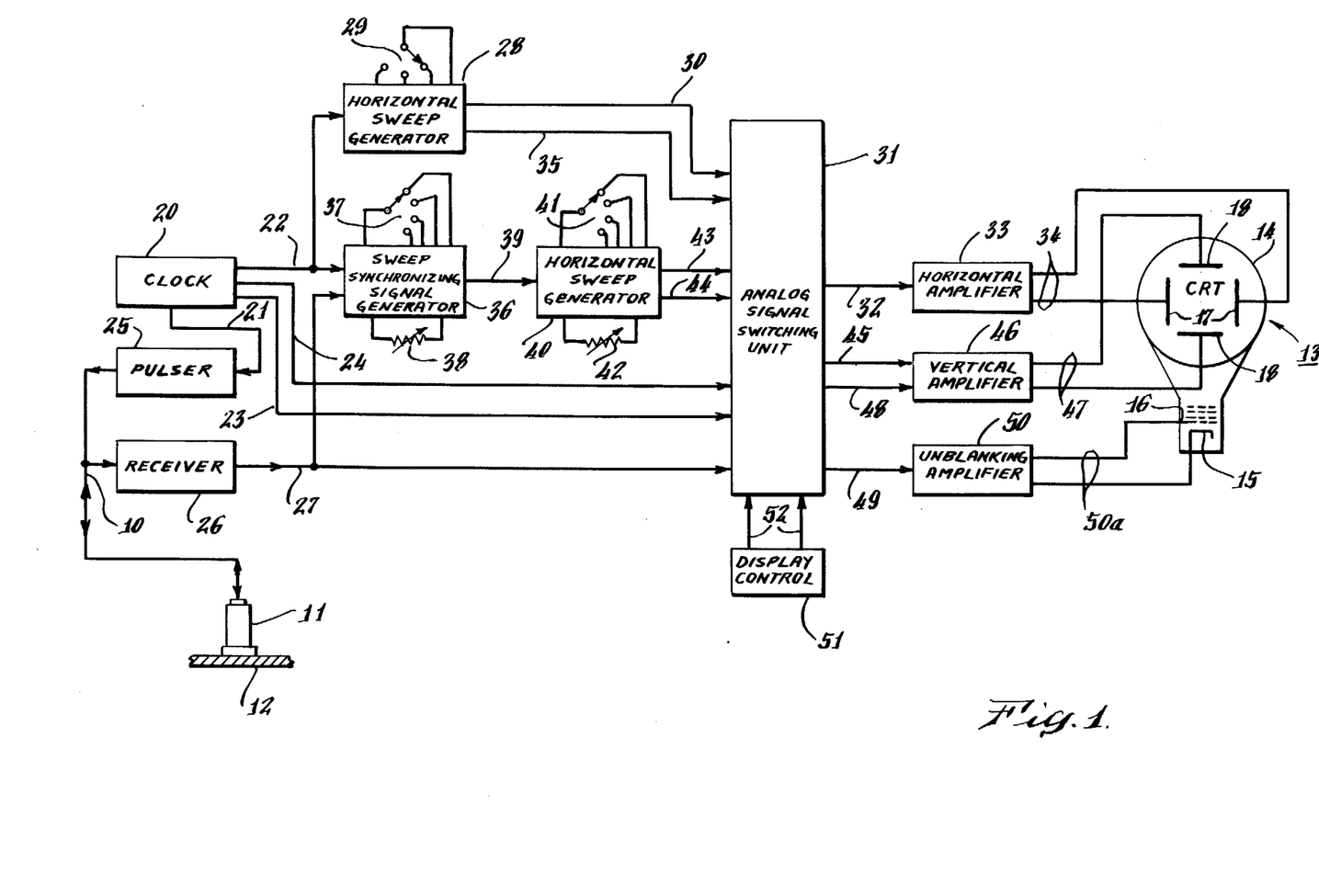
FIG. 1 is a block diagram of ultrasonic nondestructive testing apparatus embodying the present invention.

Referring now to FIG. 1 of the drawings, the present invention is particularly adapted to be embodied in ultrasonic nondestructive testing apparatus which may take any of a variety of desired forms. In the present instance it includes a transmission line, such as a coaxial cable 10, connected to transducer means, such as a search unit 11, adapted to be scanned across the surface of a workpiece 12 which is to be inspected for internal defects and other anomalies. The search unit 11 may be placed in direct, intimate contact with the surface of the workpiece 12 or it may be separated therefrom by a delay block, a water path, or the like. The search unit 11 is adapted to transmit pulses or bursts of ultrasonic energy into the workpiece 12 in response to repetitive electrical pulses. In addition, the search unit 11 is adapted to receive echoes or reflections of ultrasonic energy returned from within the workpiece 12 and to produce an electrical signal responsive to reflected ultrasonic energy.

In order to produce a visual display of test signals, the apparatus includes a conventional cathode-ray tube or oscilloscope 13 having a fluorescent viewing screen 14 and a cathode 15 for projecting a beam of electrons toward viewing screen 14. A control grid 16 is provided so that the intensity of the beam of electrons can be controlled. Cathode-ray tube 13 further includes a pair of horizontal deflection elements or plates 17 and a pair of vertical deflection elements or plates 18. As will be more apparent from the discussion to follow, cathode-ray tube 13 is utilized to provide one or more horizontal sweeps across viewing screen 14 as a function of time while vertical displacement is a function of the amplitude of test signals.

A clock generator 20 may be provided for controlling and synchronizing the operation of the entire apparatus. Clock 20 is normally a free-running pulse generator, having a frequency on the order of 1 kilocycle. However, the frequency of the clock pulses is not believed to be particularly critical. In the present instance clock 20 includes a plurality of outputs 21, 22, 23 and 24 which provide repetitive signals having a predetermined timing relationship to one another. Output 21 of clock 20 is coupled to the control input of a transmitter or pulser 25 of conventional construction whose output is coupled to search unit 11 by the flexible coaxial cable 10. The pulser 25 is responsive to the clock pulses and is effective to produce a driving pulse each time a clock pulse occurs on output 21. The driving pulse is suitable for energizing the search unit 11 and causing it to transmit a corresponding pulse or burst of ultrasonic energy, the frequency of which is not believed to be particularly critical; it may be in a range from less than 0.25 magahertz up to 25 megahertz or higher. The search unit 11 normally includes a transducer such as a piezoelectric crystal that is effective to transmit or radiate ultrasonic energy in response to an electrical driving signal and to generate an electrical signal in response to reflected ultrasonic energy that is incident on the face of the search unit. Ultrasonic energy is thus transmitted into the workpiece 12, and ultrasonic energy is reflected to the search unit 11 and particularly by the front surface, the rear surface and any flaws, defects or other characteristics which may be disposed between the two surfaces of workpiece 12. In response to reflected ultrasonic energy, the search unit 11 produces a corresponding sequence of electrical or test signals which represent the various echoes of ultrasonic energy.

To search unit 11 is coupled by means of the coaxial cable 10 to a conventional receiver 26 which is effective to receive, amplify and detect or rectify the input signals to form a video signal at receiver output 27.

In order to produce a display of the video signals at output 27, the apparatus further includes a horizontal sweep or saw-tooth wave generator 28 of conventional construction having its control circuit connected to clock output 22 which provides recurrent pulses coincident with or very slightly in advance of the recurrent pulses at clock output 21. Thus, the sweep generator 28 is triggered at essentially the same time pulser 25 generates a driving pulse and the resultant sweep signal appears at sweep generator output 30. Output 30 is connected to an analog signal switching unit 31, to be described more fully hereinafter, and, after processing, sweep signals at output 32 of unit 31 are supplied to a conventional horizontal amplifier 33 connected by leads 34 to horizontal deflection plates 17 of cathode-ray tube 13. Sweep generator 28 also provides a sweep unblanking signal at its output 35 which is coupled to unit 31.

The apparatus further includes a sweep synchronizing signal generator 36 having its control circuit connected to clock output 22 and provided with a selector switch 37 and a delay control, such as a variable resistor 38. Synchronizing signal generator 36 is also coupled to video output 27 of receiver 26. By means of control 37 synchronizing signal generator 36 may be adjusted to provide trigger pulses coincident with recurrent pulses developed by pulser 25 or with interface signals received by transducer 11. In addition, generator 36 may be adjusted so that it derives pulses delayed from interface pulses, or subject to other delays. Control 38 provides the means for selectively adjusting the amount of delay between pulses at clock output 22 and the pulses which appear at sweep synchronizing signal generator output 39. Output 39 is connected to another sweep or saw-tooth wave generator 40 similar to sweep generator 28 and provided with a sweep slope control 41 and a vernier slope control, such as a variable resistor 42. The output 43 of sweep generator 40 is connected to signal switching unit 31 so that in proper sequence the saw-tooth wave from sweep generators 28 and 40 are supplied over output 32 to horizontal amplifier 33. A sweep unblanking signal which appears at output 44 of generator 40 is also supplied to signal switching unit 31.

Video output 27 of receiver 26 is coupled to signal switching unit 31 and, in turn, video output 45 of unit 31 is connected to the input of a vertical deflection amplifier 46 which may be in the form of a differential cascode amplifier, or of other conventionl construction, having its output leads 47 connected to the vertical deflection plates 18 of cathode-ray tube 13. An offset signal output 48 is also connected to the input of vertical amplifier 46 for shifting the display vertically as the switching unit 31 shifts between the outputs of sweep generators 28 and 40.

Display enabling pulses of square wave form are provided at outputs 23 and 24 of clock 20 which are connected to switching unit 31. These enabling pulses have a 50% duty cycle and are of opposite polarity.

After processing in switching unit 31 sweep signals from sweep generators 28 and 40 appear in alternation at output 32 while at the same time an unblanking gate appears at output 49 of switching unit 31. Output 49 is coupled to the input of a conventional unblanking amplifier 50 whose output leads 50a are connected to the cathode 15 and control grid 16 of cathode-ray tube 13. Amplifier 50 is used to modulate the beam of electrons projected toward fluorescent screen 14 either to cut off the beam completely or to vary its intensity in accordance with the input signal to the amplifier.

A display control 51 is connected by leads 52 to signal switching unit 31 so that an operator may select either a dual-trace display mode or a single-trace display mode for presentation on the viewing screen 14 of cathode-ray tube 13.

In operation, assuming that display control 51 is set for a dual-trace presentation, in response to a pulse from pulser 25 ultrasonic energy is sent into the workpiece 12 by the search unit 11 and at the same time a horizontal sweep signal from generator 28 sweeps the electron beam across viewing screen 14 of cathode-ray tube 13 in a horizontal direction. The slope or time rate of increase of the sweep is correlated with the velocity of ultrasonic energy in workpiece 12, and, as a result, horizontal displacement on the screen 14 corresponds to distance into workpiece 12.

Figure 2:
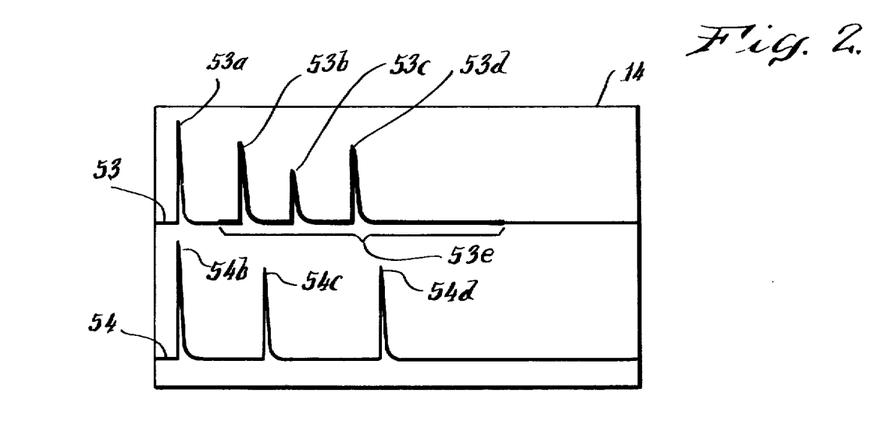
FIG. 2 is a representation of the viewing screen of the cathode-ray oscilloscope shown in FIG. 1 in one mode (the set-up mode) of operation of the apparatus embodying the present invention.

The test signal developed by search unit 11 is detected and amplified in receiver 26 and supplied to vertical amplifier 46 while the saw-tooth wave is sweeping the electron beam across the screen 14, and, thus, vertical deflection occurs in response to the test signal. At the same time, the offset signal at output 48 of switching unit 31 produces a vertical displacement of the electron beam so that a trace 53 as shown in FIG. 2 appears in approximately the upper half of screen 14.

Thus, a visual display is generated which represents the test results comprised of the burst of ultrasonic energy transmitted at the time the search unit is energized and represented by pulse 53a followed by a series of echoes represented by pulses 53b, 53c and 53d of trace 53.

Very shortly after the immediately following pulse supplied by pulser 25 to search unit 11, the sweep signal from sweep generator 40 is supplied to horizontal amplifier 33 thereby to initiate another horizontal sweep across the face 14 of cathode-ray 13 while the offset signal at output 48 is reduced in amplitude thus producing another trace 54 in approximately the lower half of viewing screen 14.

Since the saw-tooth sweep signal which occurs during this interval has a time rate of increase in amplitude greater than that in the preceding interval, and is delayed relative to the intitial pulse, the lower trace 54 includes representations 54b, 54c and 54d of the echoes 53b, 53c and 53d, respectively, in expanded form. Traces 53 and 54 occur in rapid alternation and thus to the operator's eye the two traces 53 and 54 appear to occur simultaneously on screen 14. Stated another way, the apparatus includes sweep means operative in synchronism with repetitive electrical pulses supplied to transducer 11 for deriving a first sweep signal having repetitive components occuring during time intervals defined by alternate pairs of the repetitive pulses and a second sweep signal having repetitive components occurring during time intervals defined by remaining pairs of the repetitive pulses, the components of one of the sweep signals have a time rate of increase in amplitude different from that of the components of the other of the sweep signals thereby to produce a dual trace display.

Figure 3:
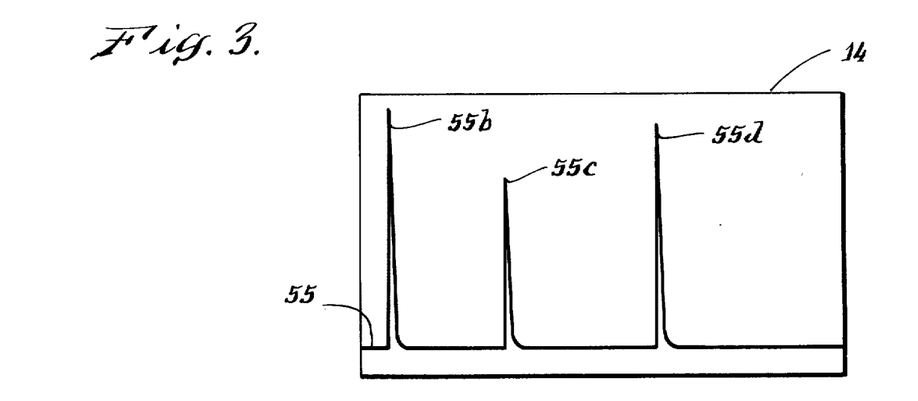
FIG. 3 shows the viewing screen represented in FIG. 2 with the apparatus in another mode (the test mode) of operation.

By manipulating display control 51, the operator may shift to another mode of operation which results in a display shown in FIG. 3 of the drawings. In this case only the sweep signal from generator 40 causes horizontal deflection of the electron beam relative to viewing screen 14 while at the same time the amplitude of the video signal supplied to vertical amplifier 46 is increased. Thus, on the face 14 of cathode-ray tube 13 there appears a single trace 55 including echo representations 55b, 55c and 55d which correspond to representations 54b, 54c and 54d shown in FIG. 2 with the same horizontal or timing relationship but of increased vertical amplitude.

Figure 4:
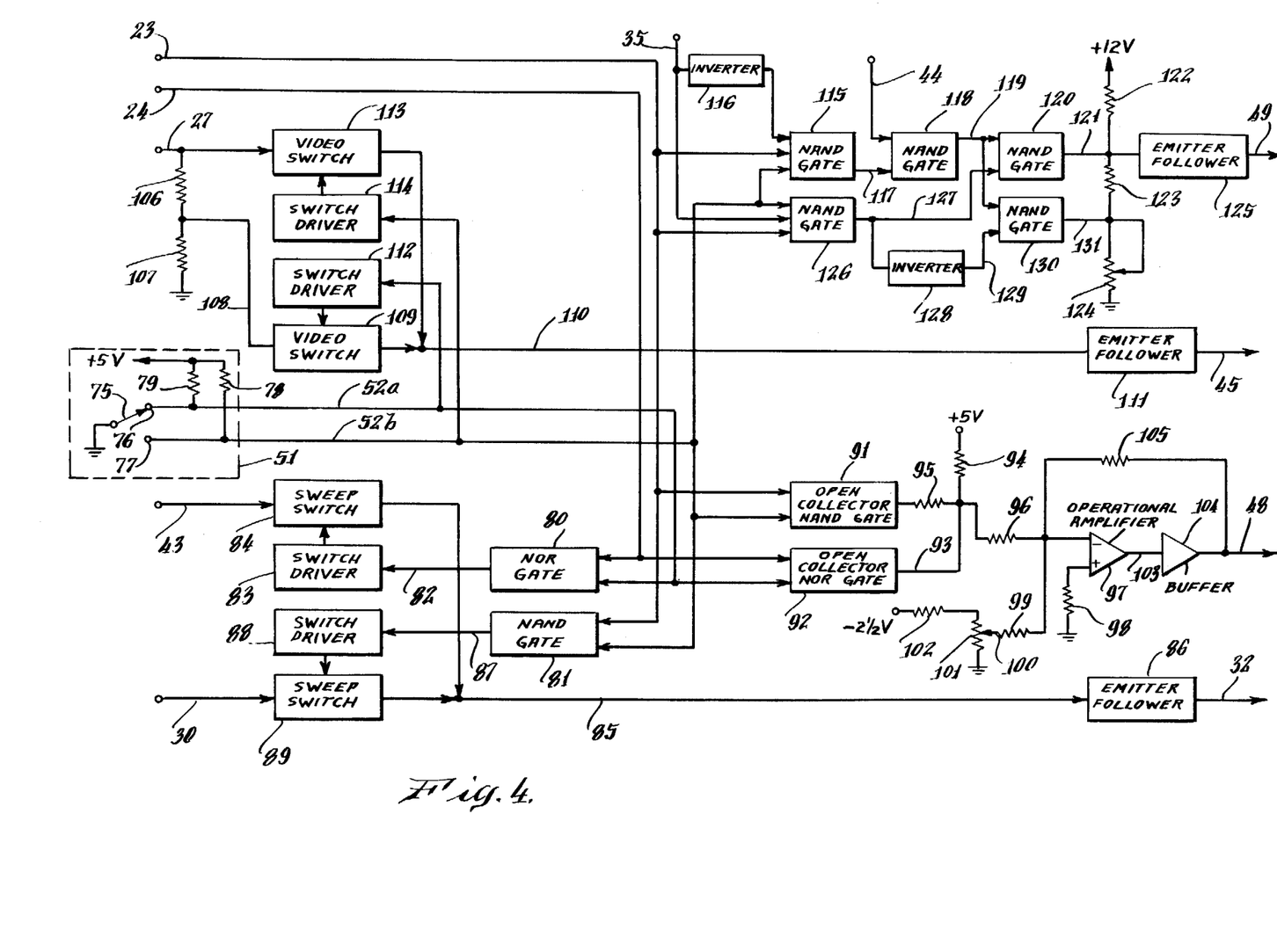
FIG. 4 is a detailed block diagram of a portion of the apparatus shown in FIG. 1.

In FIG. 4 of the drawings, certain details of the analog switching unit 31 represented in FIG. 1 are shown in block diagram form, together with a preferred form of display control 51. Display control 51 comprises a single-pole double-throw switch having its movable arm 75 grounded and its fixed contacts 76 and 77 connected through individual resistances 78 and 79 to a source of positive voltage. In addition, the contacts 76 and 77 are connected to leads 52a and 52b (represented as leads 52 in FIG. 1), in turn, connected to respective inputs of gate devices 80 and 81 of conventional construction. Gate device 80 has its remaining input connected to clock output 24 and is of the NOR type which produces a negative logic 1 signal at its output 82 only in the presence of logic 0 signals at both of its input circuits. Output 82 is connected to a conventional switch driver 83, in turn, coupled to the control circuit of a sweep switch 84 having its input connected to sweep generator output 43. Switch 84 may be of the conventional junction field effect transistor type and its output is coupled by line 85 to a conventional emitter follower 86 whose output is coupled to horizontal amplifier input 32.

Gate device 81 is a coincidence NAND gate having its remaining input connected to clock output 23 and is of the type which produces at its output 87 a logic 0 signal only in the presence of logic 1 signals at both of its input circuits. Its output is a logic 1 signal in the presence of any other combination of input signals. Output 87 is connected to another switch driver 88 similar to driver 83, in turn, coupled to the control circuit of another sweep switch 89 similar to switch 84. The input circuit of switch 89 is connected to sweep generator output 30 and its output is coupled to line 85. The portion of the circuit thus far described is operable to produce sweep signals for alternately deflecting the electron beam of cathode-ray tube 13 (FIG. 1) horizontally relative to viewing screen 14 in response to the sweep signals developed by sweep generators 28 and 40.

In order to deflect the electron beam on the face of viewing screen 14 vertically so as to produce a vertical offset during alternate sweeps, the apparatus further includes a NAND gate 91 of the open collector type having one of its input circuits connected to clock output 23 and having its remaining input circuit connected to conductor 52b. A NOR type gate 92 of the open collector type has one of its inputs connected to clock output 24 and its other input connected to conductor 52a. The output 93 of gate 92 is connected to the junction of a series resistance network 94, 95, resistance 94 being connected to a source of positive voltage, while resistance 95 is connected to the output of gate 91. The junction of resistances 94 and 95 is connected through a resistance 96 to the negative input of a conventional high gain operational amplifier 97 whose positive input is connected to ground through a resistance 98. The junction between resistance 96 and the negative input of a high gain amplifier 97 is connected through a resistance 99 to the movable arm 100 of a potentiometer 101 having one end of its resistance element grounded and the other end connected to a source of negative voltage through a resistance 102. Variable resistance 100, 101 functions as a vertical position control. Output 103 of of operational amplifier 97 is coupled to an emitter-follower type buffer 104 having its output connected to line 48. Connected between line 48 and the junction between resistances 96, 99 and the negative input of operational amplifier 97 is a feedback resistor 105. Amplifier 97, buffer 104 and feed-back resistor 105 constitute a conventional unity-gain summing amplifier.

Video output lead 27 is connected to voltage-dividing resistances 106 and 107, whose junction is connected by lead 108 to a conventional video switch device 109 having its output 110 connected to an emitter follower 111, in turn, coupled to vertical amplifier input 45. The resistance values of resistors 106 and 107 are selected so as to provide a desired amount of video signal attenuation to avoid overlap between traces 53 and 54 on screen 14. For example, attenuation of from 65% to 70% has been found to be suitable. The control circuit of video switch device 109 is connected to the output of a switch driver 112, similar to driver 83, whose input is connected to an extension of lead 52a. In the operational condition illustrated, with switch arm 75 making a connection to contact 76, attenuated video signals are supplied via emitter follower 111 to vertical amplifier 46 (FIG. 1).

Also connected to video output 27 is another video switch device 113 whose output is connected to lead 110. The control circuit of switch device 113 is connected to the output of a switch driver 114, also similar to driver 83, whose input is connected to an extension of lead 52b. When switch arm is placed into contact with electrical contact 77, video signals are supplied without attenuation to emitter follower 111 and thus to vertical amplifier 46.

Clock output 23 is also connected to one input circuit of another NAND gate 115 having another input connected to the unblanking signal output 35 of sweep generator 28 through a signal inverter 116. Output 117 of NAND gate 115 is connected to one input of yet another NAND gate 118 having its remaining input connected to sweep generator output 44. Output 119 of NAND gate 118 is connected to one input of another NAND gate 120 of the open collector type having its output 121 connected to the junction between resistances 122 and 123 of a series network which also includes a variable resistance 124. The free end of resistance 122 is connected to a source of positive voltage and the remaining terminal of resistance 124 is grounded. The junction between resistances 122 and 123 is connected to an emitter follower 125 whose output is coupled to unblanking amplifier input 49.

Clock output 23 is also coupled to one input circuit of still another NAND gate 126 having another input circuit connected to sweep generator output 35. Output 127 of NAND gate 126 is coupled to the remaining input of NAND gate 120 and to the input of an inverter 128 connected by lead 129 to the input of yet another NAND gate 130 of the open collector type. The remaining input of NAND gate 130 is coupled to output 119 of NAND gate 118. The output 131 of NAND gate 130 is connected to the junction between resistances 123 and 124.

Figure 5:
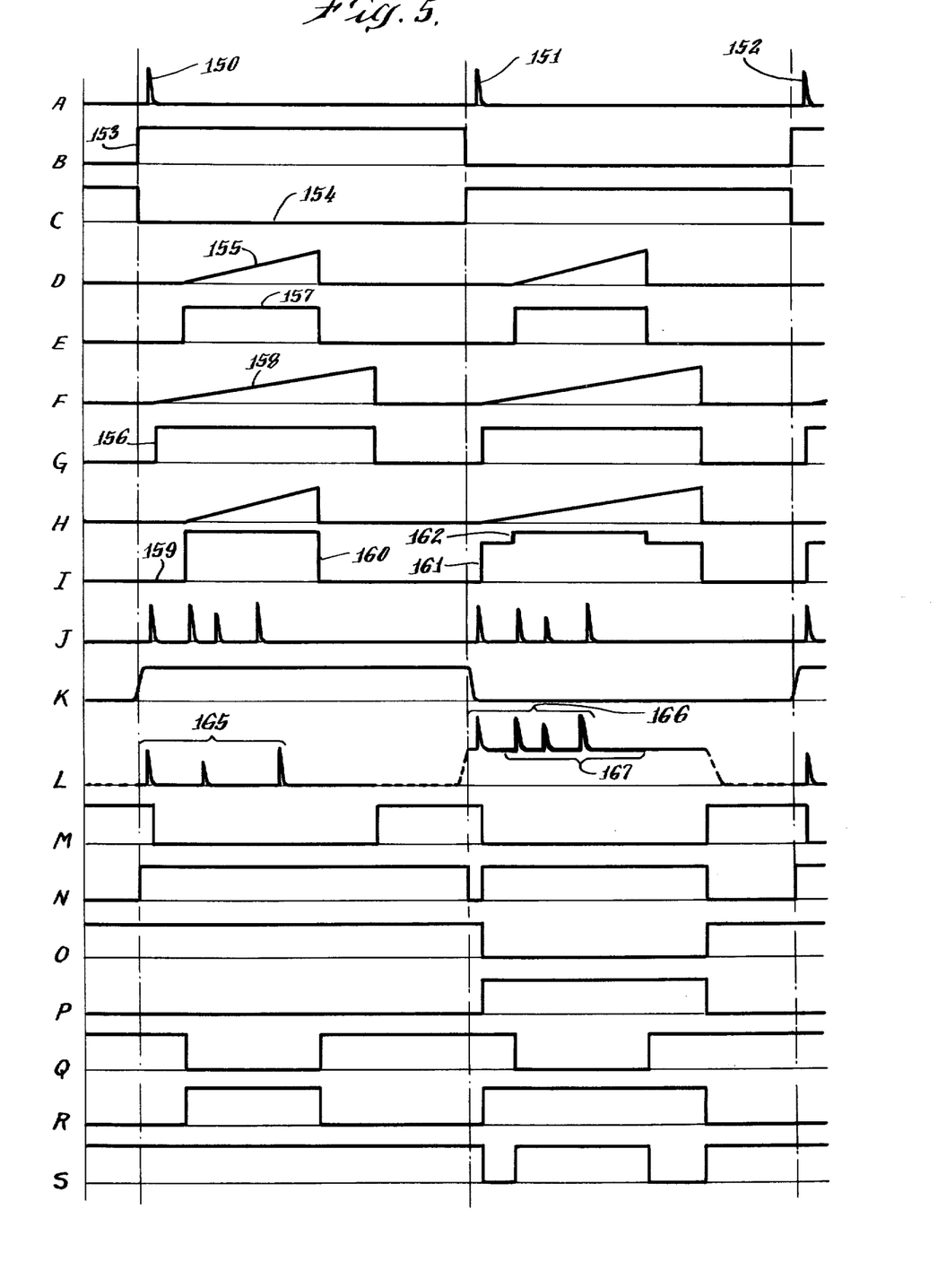
FIG. 5 is a series of wave forms of various signals which may be found in apparatus shown in FIGS. 1 and 4 adjusted in one mode of operation.

In describing the operation of the apparatus shown in FIGS. 1 and 4 and embodying the present invention, reference will by made to FIG. 5 which represents wave forms of signals that appear at various points in the apparatus, plotted to the same time scale. FIG. 5 illustrates a mode of operation in which display control 51 is in the condition shown in FIG. 4, namely, positioned for dual trace presentation.

FIG. 5A illustrates the repetitive pulses supplied by pulser 25 to search unit 11 under the control of the pulses which appear at output 21 of clock 20. Although only three such output pulses 150, 151 and 152 are shown, it is to be understood that these pulses are repetitive and continuous. Pulses 150 and 151 represent one of many alternate pairs and pulses 151 and 152 one pair of many pairs of remaining repetitive pulses.

The signal at clock output 24 is in the form of a square wave 153 illustrated in FIG. 5B. Each half cycle of square wave 153 has the same duration as the time between repetitive pulses 150, 151 and 152; however, square wave 153 is initiated slightly in advance of the repetitive pulses 150 and 152. Another square wave 154 at clock output 23 is similar to square wave 153 but is of opposite polarity, as shown in FIG. 5C.

Sweep generator 40 produces a saw-toothed wave 155 as shown in FIG. 5D and in the presence of the positive half cycles of square wave 153 NOR gate 80 operates switch driver 83 which, in turn, controls switch 84 so that the saw-toothed wave 155 is supplied to emitter follower 86 thereby to produce horizontal deflection of the electron beam within cathode-ray tube 13. During alternate half cycles, NOR gate 80 conditions switch driver 83 so that switch 84 is effectively closed and the sweep signal 155 is not supplied horizontal amplifier 33. During the first of the half cycles just described NAND gate 81 is conditioned by square wave 154 so that switch driver 88 effectively closes switch 89 and thus the sweep signal at output 30 from generator 28 is not supplied to the horizontal amplifier 33. Also during the first of the half cycles just described a square wave 156 (FIG. 5G) produced at output 35 by sweep generator 28, after inversion by inverter 116 and operating together with the signal which appears at clock output 23 conditions NAND gate 115 so that in the presence of a positive half cycle of square wave 153 at output 44, NAND gate 118 is conditioned so that a sweep unblanking signal 157 of square wave form (FIG. 5E) is supplied to NAND gate 120. Thus, an unblanking signal is supplied via emitter follower 125 to unblanking amplifier 50 and a trace is permitted to appear on the face 14 of cathode-ray tube 13. In other words a visible trace of sweep signal 155 appears only during each positive half cycle of square wave 157.

During the following half cycle of operation, enabling gate 153 (FIG. 5B) causes NOR gate 80 to condition switch driver 83 so that switch 84 is carried to its off condition and thus sweep signal 155 (FIG. 5D) is not supplied to horizontal amplifier 33. At the same time, the positive half cycle of square wave 23 conditions NAND gate 81 that switch driver 88 opens switch 89 thereby to supply the sweep signal 158 (FIG. 5F) from generator 28 to emitter follower 86 and, in turn, to horizontal amplifier 33. At the same time, the positive half cycle of unblanking square wave 156 from output 35 of sweep generator 28 conditions NAND gate 126 which, in turn, conditions NAND gate 120 so that an unblanking signal corresponding to a positive half cycle of square wave 156 is supplied via emitter follower 125 to unblanking amplifier 50 so as to produce a visible trace on the face 14 of cathode-ray tube 13. Because of the presence of a positive half cycle of square wave 157 at sweep generator output 44 at NAND gate 118, further intensification occurs.

It is thus apparent that the sweep signal which is supplied to horizontal amplifier 33 is a composite of saw-toothed waves 155 and 158 in alternation or time sequence and the composite sweep wave is represented in FIG. 5H. In addition, the intensification of the beam of electrons projected toward viewing screen 14 of cathode-ray tube 13 is under the control of a composite wave comprised of square waves 156 and 157 and the composite wave 159 is illustrated in FIG. 5I. As shown, during the first of the half cycles referred to earlier, square wave 159 includes a positive portion 160 which corresponds in timing to the square wave 157 (FIG. 5E) and during the next of the half cycles, square wave 159 includes a positive portion 161 which corresponds in timing to the positive half cycles of square wave 156. In addition, positive portion 161 includes a section 162 of slightly greater amplitude having the same duration and timing relationship to successive cycles as the alternations in square wave 157.

Resistance network 106, 107 produces attenuated video signals, represented in FIG. 5J, supplied via switch 109 to emitter follower 111, and, in turn, to vertical amplifier 46 only when switch 75–77 of control 51 is in the condition illustrated. In addition, since square waves 153 and 154 are supplied to NOR gate 92 and NAND gate 91, respectively, a square wave signal of the form illustrated in FIG. 5K is supplied to vertical amplifier 46. Thus, a composite vertical deflection signal is derived comprised of the echo signals of FIG. 5J and the square wave of FIG. 5K and composite sweep signal, as represented in FIG. 5L, produces vertical deflection of the electron beam on the face of cathode-ray tube 13. The composite signal includes a first section 165 and a second section 166 which occur in alternation. Since, as explained earlier, during the first of the two half cycles, the horizontal sweep signal 155 produces horizontal deflection and the electron beam is unblanked during the positive cycle of square wave 157, section 165 is represented as including a portion of the echo information shown in section 166, effectively expanded in time.

It is thus apparent that by virtue of the composite signal represented in FIG. 5L horizontal traces are developed on viewing screen 14 of cathode-ray tube 13 which are vertically displaced from one another in alternation. Further, because of the presence of section 162 in portion 161 of square wave 159 (FIG. 5I), an intensified portion 167 is produced in section 166 representing the time duration of the sweep of section 165. Since sections 165 and 166 of the composite signal occur rapidly and in alternation, the operator "sees" the dual trace display illustrated in FIG. 2.

For a better understanding of the operation of the various gate devices, reference will now be made to the remaining wave forms illustrated in FIG. 5. After inversion in inverter 116, square wave 156 appears as shown in FIG. 5M and that square wave is supplied to one of the inputs of NAND gate 115. Square wave 154 (FIG. 5C) is applied to another input of gate 115 and yet another input is connected to switch contact 77. The signal at output 117 of gate 115 is a square wave type signal (shown in FIG. 5N) supplied to one of the inputs of gate 118 having at its other input the square wave signal 157 shown in FIG. 5C. NAND gate 126 produces at its output 127 a square wave type signal shown in FIG. 5O and after inversion in inverter 128 that signal appears as shown in FIG. 5P. NAND gate 118 produces at its output 119 the square wave type signal represented in FIG. 5Q and the output 121 of NAND gate 120 appears in square wave form as shown in FIG. 5R. Finally, gate 130 produces at its output 131 a square wave type signal as shown in FIG. 5S.

As explained hereinbefore, the sweeps must be alternated to the horizontal amplifier 33 to create the dual-trace display. Therefore, the NOR gate 80 turns on the sweep switch 84 during the time when gate signal 153 is at the logic 1 level and the NAND gate 81 will route the sweep signal 158 through the switch 89 during the time when the gate 154 is at logic 1. The resulting sweep signal (FIG. 5H) to the horizontal amplifier consists of sweep 155 and sweep 158 alternating with each repetition rate clock pulse. The unblanking circuit generates a sweep unblanking signal with a sweep unblanking pedestal 157 during the alternate trace time. This is accomplished by controlling the logic status of the two open-collector NAND gates 120 and 130. If gate output 121 is conducting, then the unblank gate will fully blank the amplifier 50. When only gate output 131 is conducting, the unblank gate output level corresponds to the region or regions of unintensified unblanking on the upper trace 53. When both gate outputs 121 and 131 are not conducting, the output level will be even greater and corresponds to the region of intensified brightness on the upper trace. The control 124 may be used to vary the intensified brightness level from no brightup to maximum brightup.

In order to place the apparatus embodying the present invention in a single trace mode of operation, switch arm 75 of control unit 51 is displaced away from contact 76 into electrical connection with contact 77. The apparatus is thus conditioned to display only a single trace, corresponding to the lower trace 54 shown in FIG. 2, as represented in FIG. 3.

Figure 6:
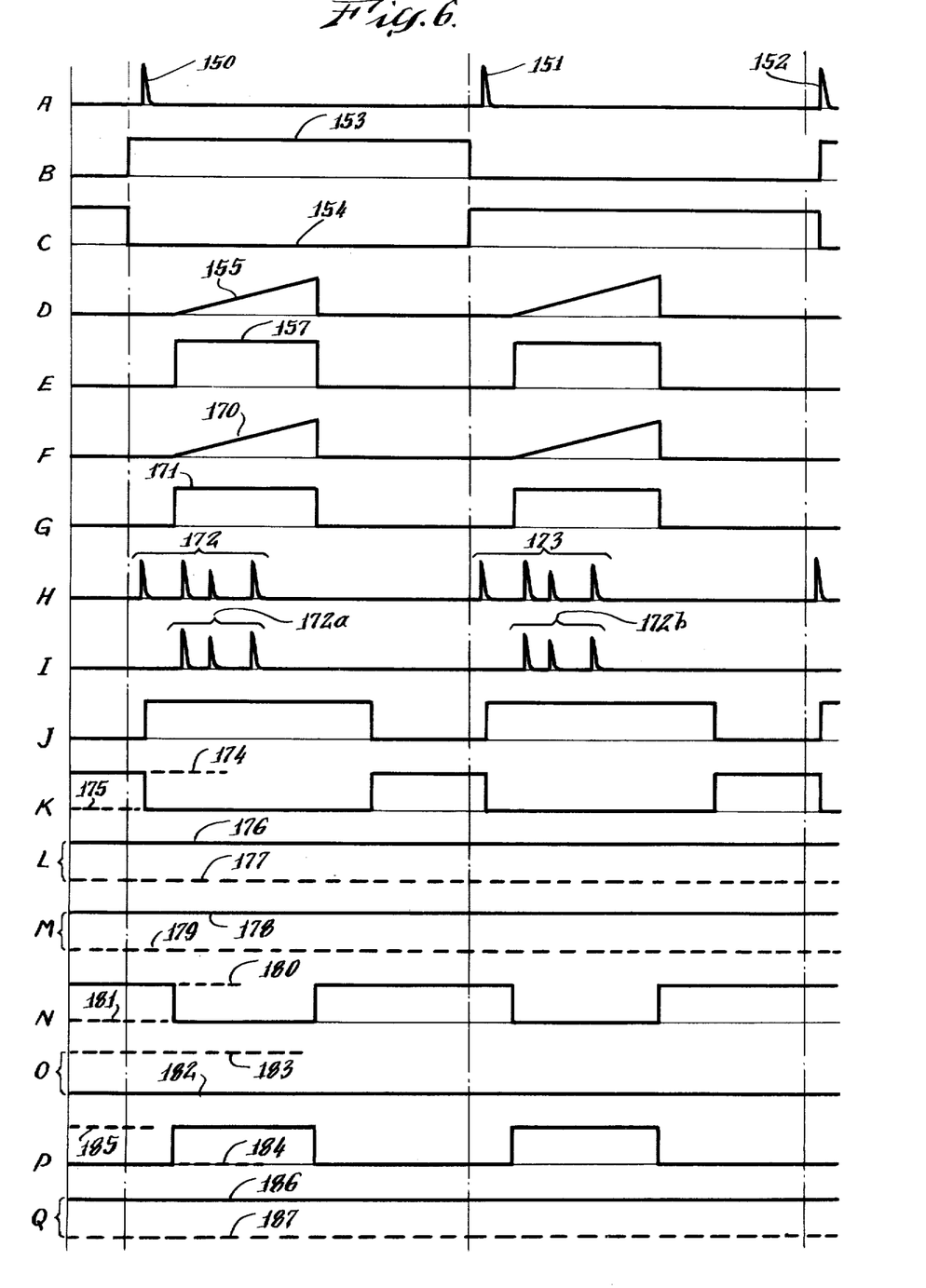
FIG. 6 is another series of wave forms, similar to that shown in FIG. 5, but illustrating another mode of operation.

FIG. 6 includes a representation of various wave forms plotted to the same time scale illustrating various signals which appear in the apparatus. FIGS. 6A through 6E of FIG. 6 are identical to the representations of FIGS. 5A through 5E, respectively of FIG. 5.

With the control switch 75–77 in the position just described, gates 80 and 81 condition the switches 84 and 89 so that only the sweep signal at output 43 is supplied via emitter follower 86 to horizontal amplifier 33. That signal is represented by the saw-toothed wave 170 shown in FIG. 6F. Further, the gates 115, 126, 118, 120 and 130 are so conditioned that an unblanking signal represented by square wave 171 in FIG. 6G is supplied to emitter follower 125. That signal is, in turn, supplied to unblanking amplifier 50. Video switches 109 and 113 are so conditioned as to supply video signals from output 27 without attenuation to emitter follower 111 and thence to vertical amplifier 46.

At the same time sweep signal 170 (FIG. 6F) is supplied to horizontal amplifier 33, unblanking signal 171 (FIG. 6G) is supplied via emitter follower 125 to unblanking amplifier 50. Unattenuated video signals which appear in successive groups, such as the groups 172 and 173 represented in FIG. 6H are supplied via emitter follower 111 to vertical amplifier 46. Because of the presence of unblanking signal 171 (FIG. 6G) only portions 172a and 172b, as shown in FIG. 6I, appear on viewing screen 14 of cathode-ray tube 13 thereby to produce the dispaly illustrated in FIG. 3.

In order better to understand the function of the various gates, reference will now be made to the remaining wave forms illustrated in FIG. 6. The unblanking gate at output 35 of sweep generator 28 is illustrated in FIG. 6J and after inversion in inverter 116 the resulting square wave type signal shown in FIG. 6K is applied to one input of NAND gate 115. The square wave of FIG. 6K varies between voltage levels indicated by reference numerals 174 and 175, but under the conditions of this mode of operations, output 117 of gate 115 produces a unidirectional voltage output having a logic 1 level denoted in FIG. 6L by reference numeral 176 having a given magnitude as compared with logic 0 level denoted by numeral 177. Output 127 of NAND gate 126 exhibits a unidirectional logic 1 level denoted in FIG. 6M by reference numeral 178, shown with reference to a logic 0 level denoted by numeral 179. The signal at output 119 of NAND gate 118 is of square wave form represented in FIG. 6N shown in relation to a negative reference 181. Output 129 of inverter 128 is illustrated in FIG. 6O as a negative unidirectional voltage 182 with reference to a level 183. The output 121 of NAND gate 120 is of square wave form illustrated in FIG. 6P varying between logic 1 level denoted by numeral 185 with reference to a logic 0 level denoted by reference numeral 184. Output 131 of NAND gate 130 is of unidirectional form as represented in FIG. 6Q having a logic 1 level denoted by numeral 186 with reference to a logic 0 level denoted by numeral 187.

With the switch 75–77 set for the single-trace mode, the switch 109 for attenuated video is turned off, and the switch 113 for unattenuated video is turned on continuously, thus allowing unattenuated video to be routed to the vertical amplifier 46. The output of NAND gate 81 to the switch driver 88 will be forced to the logic 1 state in this mode, thus turning off the switch 89. Since only sweep signal 155 is required for the single trace display, the output of NOR gate 80 to the switch driver 83 will force the switch 84 to be on, thus allowing sweep signal 155 to be routed to the horizontal amplifier 33 thereby to produce horizontal sweeps on the screen 14 of cathode-ray tube 13. To generate single trace unblanking, the NAND gate 130 with output 131 is non-conducting, thus setting the maximum amplitude for unblanking intensity, while the other NAND gate 120 output 121 is switching on and off, as shown in FIG. 6P to pull the junction between resistors 123 and 124 to zero volts for the blanked condition. The resulting unblanking signal (FIG. 6G) is supplied to the unblanking amplifier 50. Since shifting is not required in this mode, the open-collector NOR gate 92 is turned on, thus providing a zero volt input to the summing amplifier 97, 104 which biases the vertical amplifier 46 at a given level. Position control sums its level into the summing amplifier 97, 104 to produce a variable level for vertical trace positioning.

In a typical way of utilizing apparatus embodying the present invention, initially the apparatus is conditioned for dual trace presentation, and this is accomplished by displacing switch arm 75 into electrical connection with contact 76. Thus, a display such as illustrated in FIG. 2 is produced on viewing screen 14 of cathode-ray tube 13. Depending upon the type, size and condition of the test object 12, the operator may selectively provide one of several rates at which the electron beam is swept across the face of cathode-ray tube screen 14 during the interval in which trace 53 is developed. This is accomplished by adjusting control 29 of sweep generator 28. Further, the operator may position control 37 of synchronizing signal generator 36 to determine the moment in time at which the trace 54 is initiated. For example, initiation may be caused to occur with the initial pulse. Alternatively, initiation could be caused to occur with the first echo that is received by the transducer 11. Ordinarily, the first echo is caused by the interface between the face of the transducer and the surface of the test object into which it has been placed in contact. Still further, a given amount of delay may be interposed before initiation and by means of variable resistor 38 the amount of delay may be adjusted as desired. In addition, by means of control 41 the time rate of increase or the slope of the saw-toothed wave generated by sweep generator 40 may be adjusted in steps and by means of vernier control 42 a fine adjustment of slope may be made. Control 37 of synchronizing generator 36 and controls 41 and 42 of sweep generator 40 may be employed to adjust the time of initiation and the duration of the trace 54. At the same time, as discussed hereinbefore, the intensified region 53e of upper trace 53 will be positioned along the trace so as to indicate precisely the time of initiation and duration of trace 54. After the operator is satisfied that he has located a region of interest, control switch 75 may be manipulated to bring switch arm 75 into electrical connection with contact 77 thereby to produce the display represented in FIG. 3 of the region of interest alone. In this single trace mode of operation, the video signals are displayed without attenuation and thus the vertical scale of the echoes shown in FIG. 3 is expanded as compared with the vertical scale of trace 54 shown in FIG. 2.

While a single embodiment of the present invention is disclosed, it will be readily apparent to those skilled in the art that numerous changes and modifications may be made thereto without departing from the spirit of the invention. Switching devices of various types may be substituted for the electronic switch arrangements illustrated in FIG. 4. Moreover, any of the variety of coincidence and anticoincidence devices may be substituted for the NAND and NOR gates described in conjunction with FIG. 4. Accordingly, the scope of the present invention is only defined by the scope of the following claims.

I claim:

1. An ultrasonic nondestructive testing instrument for use with transducer means adapted to transmit ultrasonic energy into a workpiece in response to an electrical signal and for deriving an electrical signal in response to ultrasonic energy reflected from within the workpiece, said instrument comprising:

a cathode-ray display device including an image-producing screen, means for projecting a beam of electrons toward said screen, beam-control means and means for deflecting said beam of electrons relative to said screen in first and second directions;

sweep means operative in synchronism with repetitive electrical pulses supplied to the transducer means for deriving a first sweep signal having repetitive components occurring during time intervals defined by alternate pairs of said repetitive pulses and a second sweep signal having repetitive components occurring during time intervals defined by remaining pairs of said repetitive pulses, said components of one of said sweep signals having a time rate of increase in amplitude different from that of said components of the other of said sweep signals;

means coupling said sweep means to said deflecting means for effecting deflection of said electron beam in said first direction relative to said screen;

means for supplying an electrical signal to said deflecting means for effecting deflection of said electron beam in said second direction relative to said screen in response to electrical signals from the transducer means;

means coupled to said last-named means for deriving an offset signal in synchronism with said repetitive pulses having one amplitude during said repetitive components of said first sweep signal and another amplitude during said repetitive components of said second sweep signal to deflect said electron beam in said second direction relative to said screen between two sections thereof displaced from one another in said second direction thereby to produce a display of reflected-energy signals in each of said sections; and means coupled to said beam-control means for deriving a trace-modifying signal having components representing said repetitive components of said second sweep signal, and occurring during said repetitive components of said first sweep signal thereby to modify a portion of the display of reflected-energy signals in one of said sections of said screen in relation to the time duration of the display in the other of said sections.

2. An ultrasonic nondestructive testing instrument for use with transducer means adapted to transmit ultrasonic energy into a workpiece in response to an electrical signal and for deriving an electrical signal in response to ultrasonic energy reflected from within the workpiece, said instrument comprising:

a cathode-ray display device including an image-producing screen, means for projecting a beam of electrons toward said screen and means for deflecting said beam of electrons relative to said screen in first and second directions;

sweep means operative in synchronism with repetitive electrical pulses supplied to the transducer means for deriving a first sweep signal having repetitive components occurring during time intervals defined by alternate pairs of said repetitive pulses and a second sweep signal having repetitive components occurring during time intervals defined by remaining pairs of said repetitive pulses, said components of one of said sweep signals having a time rate of increase in amplitude different from that of said components of the other of said sweep signals, and said sweep means including means for controlling the time of initiation and the time rate of increase in amplitude of said repetitive components of said second sweep signal;

means coupling said sweep means to said deflecting means for effecting deflection of said electron beam in said first direction relative to said screen;

means for supplying an electrical signal to said deflecting means for effecting deflection of said electron beam in said second direction relative to said screen in response to electrical signals from the transducer means; and means coupled to said last-named means for deriving an offset signal in synchronism with said repetitive pulses having one amplitude during said repetitive components of said first sweep signal and another amplitude during said repetitive components of said second sweep signal to deflect said electron beam in said second direction relative to said screen between two sections thereof displaced from one another in said second direction thereby to produce a display of reflected-energy signals in each of said sections.

3. An ultrasonic nondestructive testing instrument for use with transducer means adapted to transmit ultrasonic energy into a workpiece in response to an electrical signal and for deriving an electrical signal in response to ultrasonic energy reflected from within the workpiece, said instrument comprising:

a cathode-ray display device including an image-producing screen, means for projecting a beam of electrons relative to said screen in first and second directions;

a first sweep generator operative in synchronism with repetitive electrical pulses supplied to the transducer means for deriving a first sweep signal having repetitive components of one duration;

a second sweep generator operative in synchronism with said repetitive pulses for deriving a second sweep signal having repetitive components of another duration different from said one duration;

means for coupling said first and said second sweep generators to said deflecting means for effecting deflection of said electron beam in said first direction relative to said screen and including switch means and mode-control means adapted to establish one mode of operation for said switch means wherein said electron beam is deflected in said first direction in response to said first sweep signal only during time intervals defined by alternate pairs of said repetitive pulses and in response to said second sweep signal only during time intervals defined by remaining pairs of said repetitive pulses and to establish another mode of operation wherein said electron beam is deflected in said one direction only in response to one of said first and said second sweep signals;

means for supplying an electrical signal to said deflecting means for effecting deflection of said electron beam in said second direction relative to said screen in response to electrical signals from the transducer means;

means coupled to said last-named means for deriving an offset signal in synchronism with said repetitive pulses having one amplitude during said repetitive components of said first sweep signal and another amplitude during said repetitive components of said second sweep signal and operative in said one mode of operation to effect deflection of said electron beam in said second direction relative to said screen between two sections thereof displaced from one another in said second direction thereby to produce a display of reflected-energy signals in each of said sections; and selectively operable signal-attenuation means operative during said one mode of operation effectively to attenuate electrical signals supplied to said deflecting means in response to electrical signals from the transducer means.

4. An ultrasonic nondestructive testing instrument for use with transducer means adapted to transmit ultrasonic energy into a workpiece in response to an electrical signal and for deriving an electrical signal in response to ultrasonic energy reflected from within the workpiece, said instrument comprising:

a cathode-ray display device including an image-producing screen, means for projecting a beam of electrons toward said screen including beam-intensity-control means and means for deflecting said beam of electrons relative to said screen in first and second directions;

a first sweep generator operative in synchronism with repetitive electrical pulses supplied to the transducer means for deriving a first sweep signal having repetitive components of one duration;

a second sweep generator operative in syncrhonism with said repetitive pulses for deriving a second sweep signal having repetitive components of another duration different from said one duration;

means for coupling said first and said second sweep generators to said deflecting means for effecting deflection of said electron beam in said first direction relative to said screen and including switch means and mode-control means adapted to establish one mode of operation for said switch means wherein said electron beam is deflected in said first direction in response to said sweep signal only during first time intervals defined by alternate pairs of said repetitive pulses and in response to said second sweep signal only during second time intervals defined by remaining pairs of said repetitive pulses and to establish another mode of operation wherein said electron beam is deflected in said one direction only in response to one of said first and said second sweep signals;

means for supplying an electrical signal to said deflecting means for effecting deflection of said electron beam in said second direction relative to said screen in response to electrical signals from the transducer means;

means coupled to said last-named means for deriving an offset signal in synchronism with said repetitive pulses having one amplitude during said repetitive components of said first sweep signal and another amplitude during said repetitive components of said second sweep signal and operative during said one mode of operation to deflect said electron beam in said second direction relative to said screen between two sections thereof displaced from one another in said second direction thereby to produce a display of reflected-energy signals in each of said section; and means coupled to said beam-intensity-control means for deriving a trace-modifying signal having components corresponding in duration to that of said repetitive components of said second sweep signal and occurring during said repetitive components of said first sweep signal thereby to modify a portion of the display of reflected-energy signals in one of said sections of said screen in relation to the time duration of the display in the other said sections.

5. A display system for ultrasonic nondestructive testing apparatus including transducer means, a pulser for supplying repetitive electrical pulses to the transducer to transmit ultrasonic energy into a workpiece and a receiver coupled to the transducer means to derive reflected-energy signals in response to ultrasonic energy reflected from within the workpiece, said system comprising:

a cathode-ray tube including an image-producing screen, means for projecting a beam of electrons toward said screen and means for deflecting said beam of electrons relative to said screen in first and second directions;

sweep generator means operative in synchronism with the repetitive electrical pulses supplied to the transducer means for deriving a first sweep signal having repetitive components occurring during time intervals defined by alternate pairs of said repetitive pulses and a second sweep signal having repetitive components occurring during time intervals defined by remaining pairs of the repetitive pulses, said components of one of said sweep signals having a time rate of increase in amplitude different from that of said components of the other of said sweep signals;

means coupling said sweep generator means to said deflecting means for effecting deflection of said electron beam in said first direction relative to said screen;

means for supplying an electrical signal to said deflecting means for effecting deflection of said electron beam in said second direction relative to said screen in response to electrical signals from the receiver; and means coupled to said last-named means for deriving an offset signal in synchronism with the repetitive pulses having one amplitude during said repetitive components of said first sweep signal and another amplitude during said repetitive components of said second sweep signal to deflect said electron beam in said second direction relative to said screen between two sections thereof displaced from one another in said second direction thereby to produce a display of reflected-energy signals in each of said sections.

6. An ultrasonic nondestructive testing apparatus comprising:

a pulser for deriving repetitive electrical pulses;

a search unit including transducer means adapted to transmit ultrasonic energy into a workpiece in response to an electrical signal and for deriving an electrical signal in response to ultrasonic energy reflected from within the workpiece;

a receiver having an input circuit coupled to said search unit and having an output circuit providing a test signal responsive to said electrical signal derived by said transducer means;

a cathode-ray display device including an image-producing screen, means for projecting a beam of electrons toward said screen and means for deflecting said beam of electrons relative to said screen in first and second directions;

sweep means operative in synchronism with said repetitive electrical pulses for deriving a first sweep signal having repetitive components occurring during time intervals defined by alternate pairs of said repetitive pulses and a second sweep signal having repetitive components occurring during time intervals defined by remaining pairs of said repetitive pulses, said components of one of said sweep signals having a time rate of increase in amplitude different from that of said components of the other of said sweep signals;

means coupling said sweep means to said deflecting means for effecting deflection of said electron beam in said first direction relative to said screen;

means coupled to said output circuit of said receiver for effecting deflection of said electron beam in said second direction relative to said screen in response to said test signal; and means coupled to said last-named means for deriving an offset signal in synchronism with said repetitive pulses having one amplitude during said repetitive components of said second sweep signal to deflect said electron beam in said second direction relative to said screen between two sections thereof displaced from one another in said second direction thereby to produce a display of reflected-energy signals in each of said sections.

* * * * *